United States Patent [19]

Lacey

[11] Patent Number: 4,502,483
[45] Date of Patent: Mar. 5, 1985

[54] METHOD AND APPARATUS FOR SHAPING A DISTAL FEMORAL SURFACE

[75] Inventor: James A. Lacey, Winter Park, Fla.

[73] Assignee: Dow Corning Corporation, Midland, Mich.

[21] Appl. No.: 473,466

[22] Filed: Mar. 9, 1983

[51] Int. Cl.³ .................................... A61F 5/04
[52] U.S. Cl. .......................... 128/303 R; 128/92 E; 128/92 H
[58] Field of Search ............ 128/92 R, 92 E, 92 EA, 128/92 EB, 92 H, 305, 317, 303; 3/1.9, 1.91, 1.911

[56] References Cited

U.S. PATENT DOCUMENTS

| 4,211,228 | 7/1980 | Cloutier | 3/1.911 |
| 4,349,018 | 9/1982 | Chambers | 128/92 E |
| 4,457,307 | 7/1984 | Stillwell | 128/317 |

OTHER PUBLICATIONS

Zimmer, "Cloutier TM Total Knee" 1979, B274 5M679.
Howmedica, "The Howmedica Kinematic Knee System", 1981, ST3210-1 2/81 15MB.
Howmedica, "Total Condylar Knee Prosthesis Surg. Tech." C. S. Ranawat, 1978, ST2010 2/79 10MB.
Zimmer, "Eptekhar TM II Knee Prosthesis", 1981, B-281 5M281.
Zimmer, "Geo-Patella TM /Geo-Tibial TM Total Knee" 1977, B-260-1 10M778.
Richards, "R.C.M. TM Total Knee System" 1978, 3246, Rev 9-79.
Zimmer, "The Multi-Radius TM Total Knee with Surgeon-Guided Instrumentation" 1978 B271 7500 M 680.
Howmedica Surg. Tech., "Total Condylar Prosthesis Surg. Tech." J. N. Insall et al., 1976 ST 2002 12/76 10M.
The Howmedica ® Universal TM Total Knee Instrumentation System, Brochure No. H-2026-1 1/82 15M B (1980); Howmedica, Inc., Rutherford, NJ 07070, especially see pp. 19-24 and FIG. 14.
"New Jersey Tricompartmental Total Knee Replacement Surgical Procedure by Frederick F. Buechel, M.D.", 13 pages, issue date 1/1981, Form No. 1280-32, DePuy division, Boehringer Mannheim Corp., Warsaw, Ind., 46580.
Dow Corning Wright Knee Instrumentation System, Data Sheet No. L095-0015, dated Jan. 1982; Dow Corning Wright, Arlington, TN 38002, 6 pages.
Dow Corning Wright Lacey Condylar Total Knee System, Data Sheet No. L095-0104, ©Dow Corning Wright 1983, Arlington, TN 38002, 8 pages.

*Primary Examiner*—C. Fred Rosenbaum
*Assistant Examiner*—C. W. Shedd
*Attorney, Agent, or Firm*—Richard E. Rakoczy

[57] ABSTRACT

The present invention provides a method and apparatus for preparing the distal surface of a femur to receive a distal femoral prosthesis employing an alignment guide which is used to externally locate the central long axis of the femur based upon certain external reference points on the distal femur. The alignment guide is composed of a main body, a pivotable resection guide instrument holder, a locator pin, at least one femoral surface modifying instrument which cooperatively engages with the holder and a means such as a clamp for affixing the main body to the femur to accomplish the shaping of the distal femoral surface. The central long axis of the main body is brought into alignment with the central long axis of the femur through the use of a locator pin. The pivotable instrument holder holds resection guide instruments at a preselected angle with respect to the main body such that the shaping instruments fixed thereto assume the proper alignment with respect to the central long axis of the femur such that the distal femoral surface is shaped relative to that axis in a simple and accurate manner.

6 Claims, 17 Drawing Figures

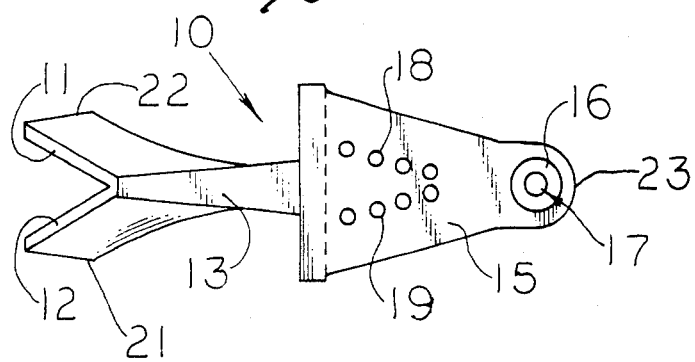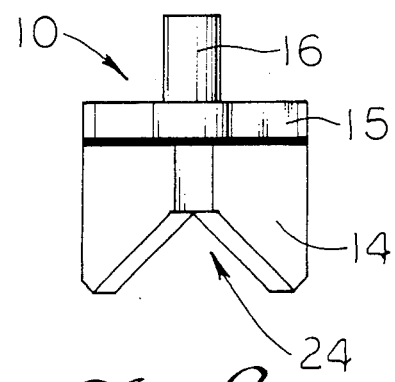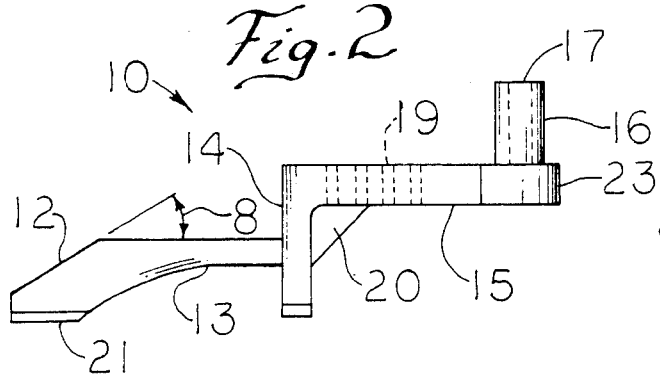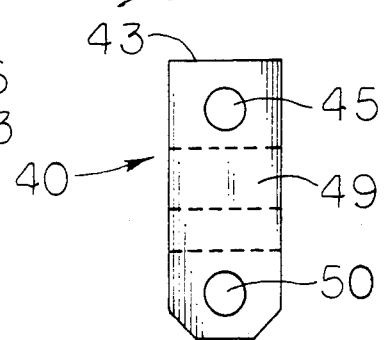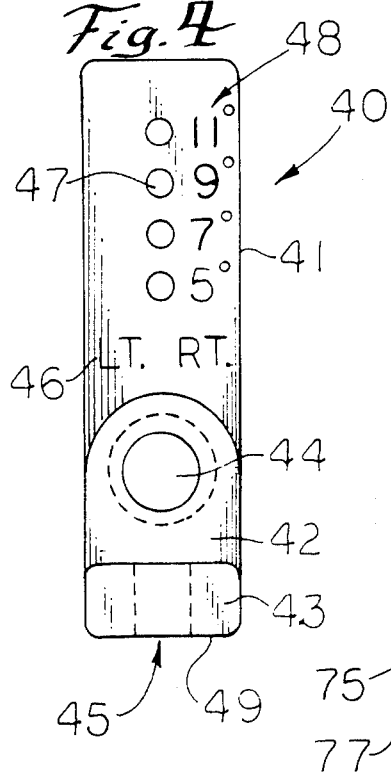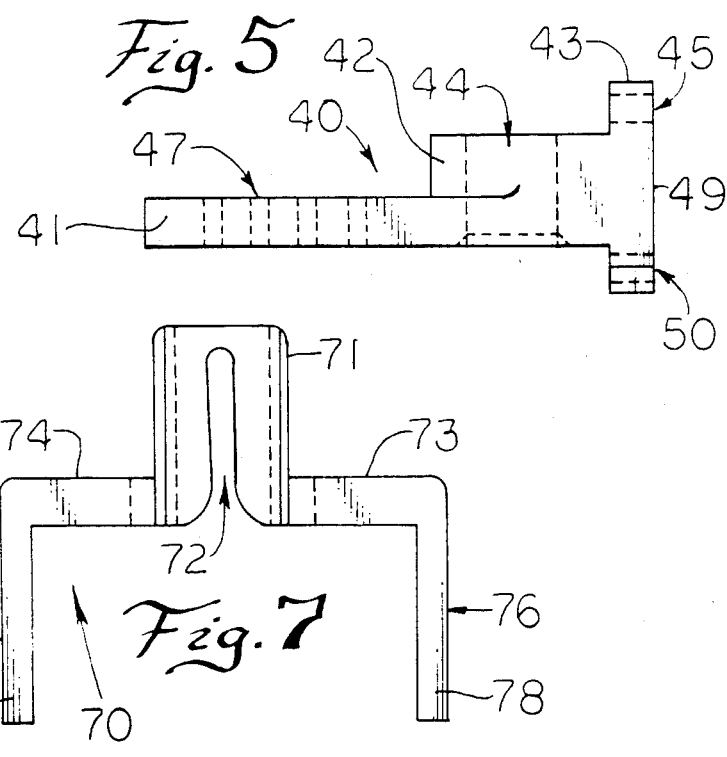

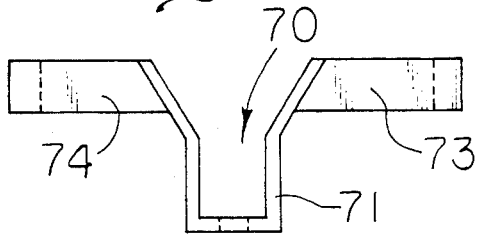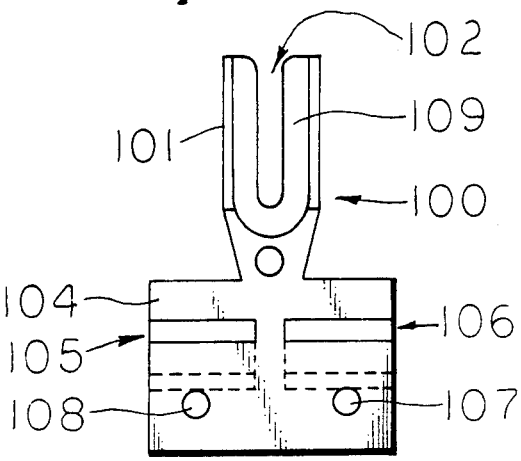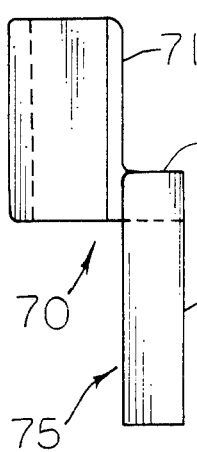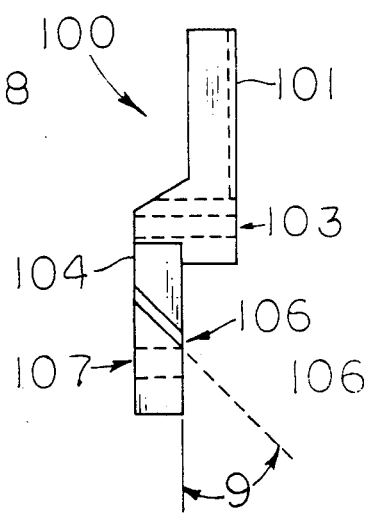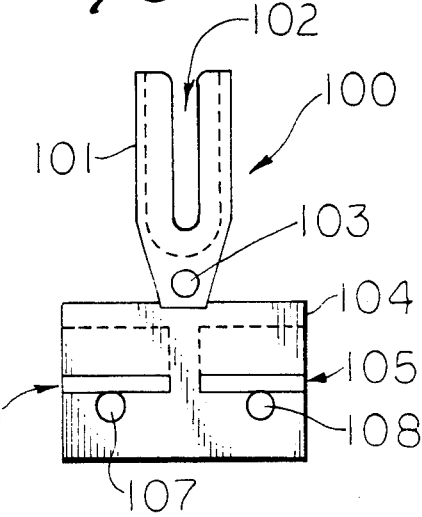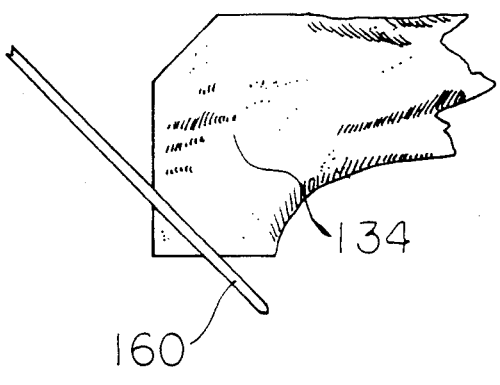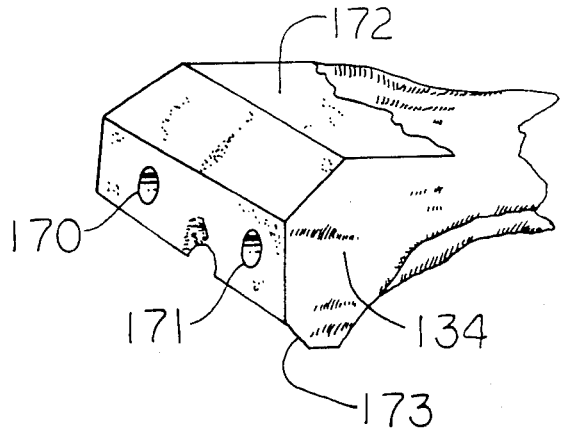

METHOD AND APPARATUS FOR SHAPING A DISTAL FEMORAL SURFACE

BACKGROUND OF THE INVENTION

This invention relates to a method of shaping the distal surface of a human femur using certain alignment guides to guide the shaping of that surface to receive a distal femoral prosthesis and to certain apparatus used in the method.

Various types of alignment guides and methods have been developed to enable a surgeon to affix a distal femoral knee prosthesis to the human femur. Since the purpose for affixing such a prosthesis is to restore the patient's ability to walk after disease or other traumatic causes have impaired that ability, it is important that the prosthesis be attached to the femur in such a manner that it will approximate as closely as possible the natural condyles which the prosthesis is replacing. If the prosthesis is not properly affixed with respect to the femur, an unnatural gait or other complications can result.

It is common practice to use the long central axis of the femur as a guide in determining the manner in which the distal femoral surface should be shaped to receive a properly aligned distal femoral prosthesis. Generally, a pre-operative single, long anterior-posterior radiograph showing the shaft of the tibia and femur is made and the angle of the long central axis of the femur relative to the vertical axis of the body (physiological valgus, generally from 5°–12°) is visualized. That angle is then used as a reference when the distal femoral surface is shaped using various cutting instruments and guides. In one such method, a long axial alignment jig (rod) is employed which is positioned over the outside surface of the patient's leg in a position which the surgeon visually determines to correspond to the central long axis of the femur and the femur is shaped relative to the alignment of that rod. One example of the manner in which the distal femoral surface is shaped to receive a prosthesis using an external alignment rod is shown in "The HOWMEDICA Universal Total Knee Instrument System", brochure no. H-2026-1 1/82 15M B (1980) from HOWMEDICA, Inc., Orthopaedics Division, Rutherford, NJ 07070 which is hereby incorporated by reference.

The external alignment rod has a disadvantage in that the surgeon is relying upon visual and tactile means for positioning the alignment rod and thereby the femoral surface resection guide since the patient's skin covers the major portion of the femur and screens it from view.

One part of the method described in the aforementioned Howmedica, Inc., brochure employs the use of a femoral drill jig having two posterior skids which align with the posterior surfaces of the femoral condyles and a drill bit which is caused to rest in the center of the patello-femoral (intercondylar) groove to obtain correct medial-lateral and rotational positioning of the jig prior to using the jig to bore holes in the femur to receive the fixation studs of a distal femoral prosthesis. Thus, reference points located directly on the distal femoral surface are employed to position the jig. However, the initial reaction of the distal femoral condyles is made using a jig employing an external alignment rod. Resection of the anterior and posterior aspects of the distal femoral condyles is accomplished through the use of another jig which has locking studs which are inserted into the fixation stud holes remaining in the femur after the femoral drill jig is removed.

A method for shaping the distal femoral surface employing the use of a relatively short femoral alignment rod which is positioned in the intramedullary canal is shown in a brochure entitled "New Jersey Tricompartmental Total Knee Replacement Surgical Procedure by Frederick F. Buechel, M.D.", 13 pages, issue date 1/1981, Form. No. 1280-32, from DePuy Division, Boehringer Mannheim Corporation, Warsaw, Ind. 46580.

In both of the above procedures, the alignment rods employed may not enable a surgeon to accurately follow the central long axis of the femur because the femur is not exposed to visual observation along its length. This can especially become a problem when the femur possesses a deformity which may somewhat alter its true central long axis.

SUMMARY OF THE INVENTION

There appears to be a need for a method of shaping the distal surface of a femur to receive a distal femoral prosthesis which enables a surgeon to shape that surface as accurately as possible using certain external reference points associated with the surface of the distal femur.

One object of the present invention is to provide a means by which certain reproducible reference points for the shaping of the distal femoral surface can be instrumentally located and fixed.

It is another object of the present invention to provide a fixed alignment guide upon which all femoral surface resection guiding instruments can be mounted such that the alignment of each instrument is always made relative to certain reference points located on the distal portion of the femur: the anterior surface of the distal portion of the femur, the intercondylar notch located between the medial and lateral distal femoral condyles, and the posterior aspects of the distal femoral condyles.

It is another object of the present invention to provide a method for overcoming the difficulties involved in attempting to externally locate the central long axis of the femur, particularly when the femur contains a deformity, and to enable a surgeon to more accurately shape the distal surface of a femur relative to that axis for the purpose of receiving a distal femoral prosthesis in a relatively simple manner.

These and other objects of the present invention are provided by a method which comprises placing a main body of an alignment guide having a resection guide instrument holder affixed thereto on the anterior surface of the femur wherein the holder is adjusted to hold a pivotable resection guide instrument at a preselected angle with respect to the central long axis of the main body and of the femur; inserting a locator pin through the pivot point of the holder; advancing the main body along the anterior surface of the femur until the locator pin contacts the center of the intercondylar notch of the distal femoral condyles; rotating the main body to properly align the central axis of the locator pin transversely with respect to the posterior aspects of the femoral condyles; affixing the main body to the femur; attaching a distal femoral surface shaping guide instrument to the instrument holder; modifying the distal femoral surface through the use of that instrument; attaching other guide instruments as needed and further modifying the distal femoral surface; removing the alignment guide; and completing any further shaping of the distal femoral surface.

This invention also relates to a distal femoral alignment guide which is a combination of a main body, an instrument holder, a locator pin, a distal femoral surface shaping guide and a means for affixing the main body to the femur.

BRIEF DESCRIPTION OF THE DRAWINGS

The above and other objects, features and advantages of the present invention will become apparent to those skilled in the art upon an examination of the following description and drawings which are merely illustrative of the present invention.

In the Drawings:

FIG. 1 is a plan view of the main body of the alignment guide of the present invention.

FIG. 2 is a side view of FIG. 1.

FIG. 3 is a front view of FIG. 1.

FIG. 4 is a plan view of a resection guide instrument holder.

FIG. 5 is a side view of FIG. 4.

FIG. 6 is a front view of FIG. 4.

FIG. 7 is a front view of a distal femoral condyle resection guide instrument.

FIG. 8 is a plan view of FIG. 7.

FIG. 9 is a side view of FIG. 7.

FIG. 10 is a rear view of an anterior-posterior distal femoral condyle resection guide.

FIG. 11 is a side view of FIG. 10.

FIG. 12 is a front view of FIG. 10.

FIG. 16 is a side perspective view of the last step in shaping a distal femoral surface in accordance with the method of the present invention.

FIG. 17 is a side perspective view of a distal femoral surface fully shaped in accordance with the method of the present invention.

DETAILED DESCRIPTION OF THE INVENTION

Figure 13:
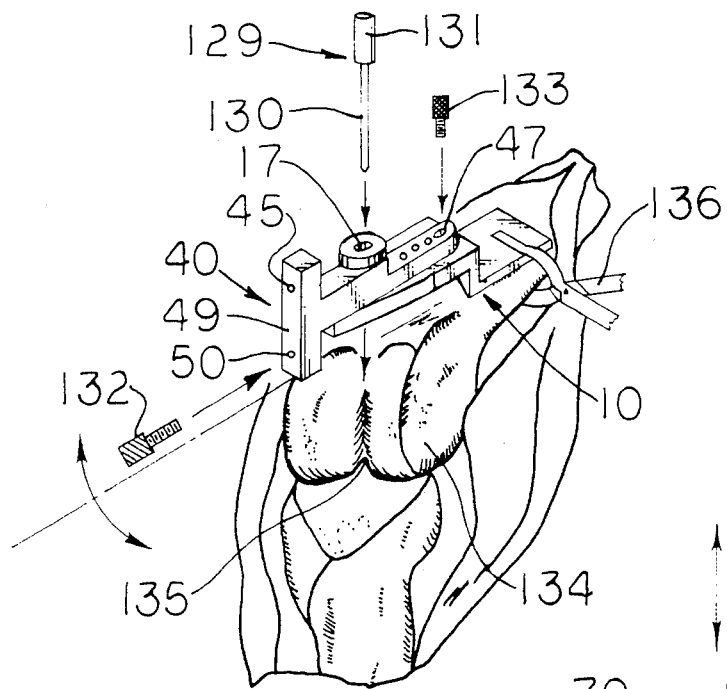
FIG. 13 is a perspective view of a human knee with the distal femur and proximal tibia exposed, further showing the main body of FIG. 1 in place, the resecting guide instrument holder of FIG. 4 in place and a locator pin.

Referring to the drawings, FIGS. 1–3 show the preferred form for the main body 10 of the alignment guide of the present invention. Main body 10 contains a pair of positioning fins 11 and 12 which are adapted to rest on the anterior surface of the shaft of the distal femur and in the embodiment shown are 0.5" (12.7 mm)—the symbol– means inches and mm means millimeters—in width at edge 21 appearing in the side view of FIG. 2. Arm 13 connects fins 11 and 12 to transverse positioning plate 14. In the preferred embodiment of FIG. 2, the distance along the upper surface of arm 13 from plate 14 to the point where fin 12 angles downward is 2" (50.8 mm), the distance from plate 14 to the distal end of fin 12 is 3" (76.2 mm), the distance between the outer edges 21 and 22 of fins 11 and 12 as shown in FIG. 1 is about 1.4" (36 mm) and the angle 8 between an extension of the upper surface of fin 12 and surface 13 is 30°. In FIG. 2, plate 14 is 1.47" (37.3 mm) high and 0.25" (6.4 mm) thick having a distance of 0.69" (17.5 mm) between the upper surface of plate 15 and the upper surface of arm 13. Arm 13 is 0.28" (7.1 mm) in thickness. In FIG. 3, plate 14 is 1.87" (47.5 mm) in width. Cylindrical guideplate holder 16 extends upward from plateau 15 and is designed to cooperatively engage with the hereinafter described resection instrument guide holder and in the preferred embodiment shown is 0.497" (12.6 mm) in diameter, 0.63" (16 mm) high and has a concentric passage 17 through its center which is transverse to and passes through plateau 15. Passage 17 is adapted to cooperatively engage a locator pin as will be described infra. In the embodiment shown in FIG. 1, passage 17 is 0.257" (6.5 mm) in diameter and the center (central long axis) of passage 17 is 0.38" (9.7 mm) from edge 23 of plateau 15. The preferred main body 10 shown in FIG. 1 is 5.63" (143 mm) in length from a vertical plane defined by the distal edges of fins 11 and 12 to the edge 23 of plateau 15, i.e., along its central long axis.

In the preferred embodiment shown in FIG. 1, four threaded passages 18 and corresponding threaded passages 19 pass through the surface of plateau 15 with the centers of passages 18 and 19 which are closest to holder 16 being a horizontal distance of 1" (24.4 mm) from the central long axis (center) of holder 16, the measurement being taken along the horizontal central long axis of main body 10, and the remainder of passages 18 and 19 are situated a horizontal distance of 1.25", 1.50" and 1.75" (31.8 mm, 38.1 mm and 44.4 mm), respectively, from that axis. Each passage is placed on plateau 15 such that when the hereinafter described resection guide instrument holder is affixed to the main body, the holder can be adjusted to hold a resection guide instrument at a fixed angle with respect to the horizontal central long axis of the upper portion of main body 10 and thereby to the central long axis of the femur which is caused to run through the horizontal central long axis of the upper portion of the main body 10 by means of the hereinafter described manner in which it is affixed to the distal femur. In the preferred embodiment shown, the centers of the closest of passages 18 and 19 to passage 17 are each typically situated 0.0435" (1.10 mm) from the horizontal central long axis of main body 10 while the remaining passages are situated 0.0765", 0.119" and 0.170" (1.94 mm, 3.02 mm and 4.32 mm), respectively, away from the central long axis (center) of holder 16. As shown in FIG. 2, a reinforcing means shown as rib 20 may be fitted between positioning plate 14 and plateau 15 to strengthen and rigidify plateau 15. All measurements specified herein are nominal.

FIG. 3 shows main body 10 from the front showing the recess 24 in positioning plate 14 which as a configuration similar to fins 11 and 12 and is likewise adapted to rest on the anterior surface of the distal femur to securely affix main body 10 to that surface. In the preferred embodiment shown, the recess 24 extends 0.5" (12.7 mm) upward in the center and the sides are set at a 45° angle with respect to a plane running across recess 24 along the bottom edge of positioning plate 14.

Figure 14:
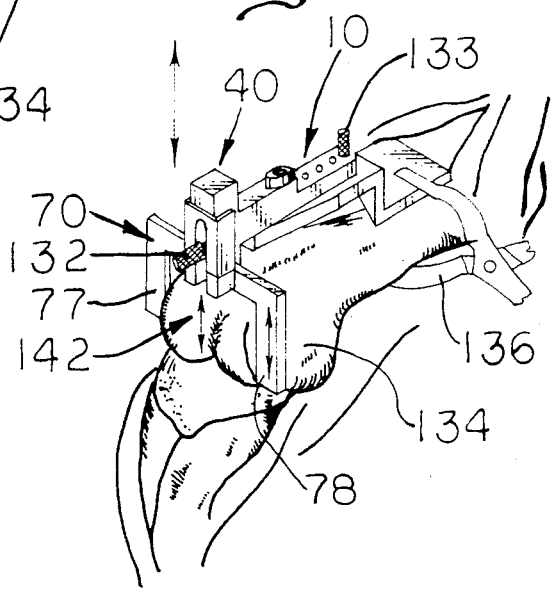
FIG. 14 is a perspective view as in FIG. 13 further having the distal femoral condyle resection guide instrument of FIG. 7 in place.
Figure 15:
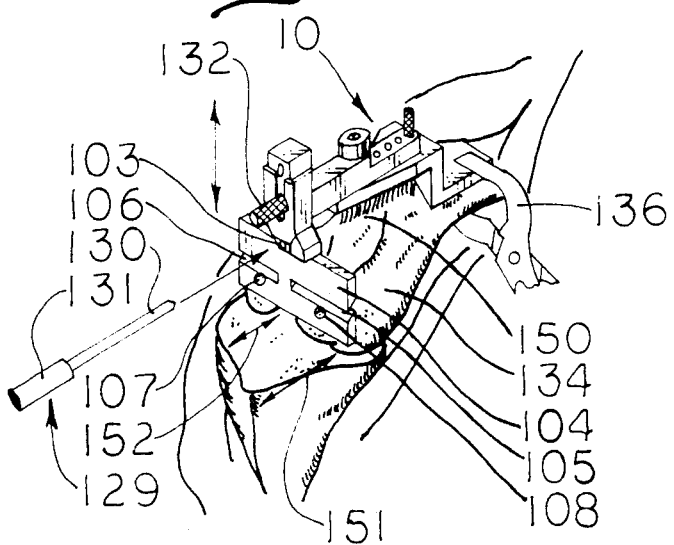
FIG. 15 is a perspective view as in FIG. 13 further having the anterior-posterior distal femoral condyle resection guide instrument of FIG. 10 in place.

FIGS. 4–6 show the preferred form for the resection guide instrument holder 40 which cooperates with the previously described main body 10 in forming the alignment guide of the present invention. Holder 40 is composed of a locator plate 41 having a raised portion 42 which cooperatively engages guideplate holder 16 of main body 10 by means of passage 44. Passage 44 fits over guideplate holder 16 and allows plate 41 to pivot about the central long axis of guideplate holder 16 to enable resection guide instruments which cooperatively engage with guideplate 43 to be pivoted about the same axis. Guideplate 43 is affixed to and forms a part of raised portion 42 and locator plate 41. When holder 40 is affixed to main body 10 as shown in FIGS. 13-15 and locator plate 41 is pivoted about the central axis of holder 16, passages 47 which are marked with numerals 48 are brought into alignment with passages 18 (for the right femur) and passages 19 (for the left femur as indicated by reference numeral 46). A locking bolt or other position fixing means can then be placed through the preselected passage 47 and corresponding appropriate passage 18 or 19 to cause the front surface 49 of guideplate 43 to assume a specific angle (5°, 7°, 9°, 11° or some other preselected angle) with respect to the horizontal central long axis of the main body 10 and thus with respect to the central long axis of the femur to shape the femur to the preselected degree of physiological valgus. As will be described infra, guideplate 43 is of a suitable configuration which enables a distal femoral surface resection guide to be cooperatively engaged with it such that the distal femoral surface is resected relative to the position of holder 40 to the horizontal central long axis of main body 10. To this end, guideplate 43 contains passages 45 and 50 which are threaded or contain some other means therein to receive a means for fixedly securing a resection guide instrument to guideplate 43.

In the preferred embodiment shown in FIGS. 4-6, passage 44 has a 0.500" (12.7 mm) inner diameter when main body 10 having holder 16 of 0.497" (12.6 mm) outer diameter is employed. The centers of passages 47 are located 0.004", 1.259", 1.519" and 1.783" (25.50 mm, 31.98 mm, 38.58 mm and 45.29 mm), respectively, from the center of passage 44. In the preferred embodiment shown, the planar surface 49 of guideplate 43 facing shown in FIGS. 5 and 6 is vertically (FIG. 5) parallel to the central long axis of passage 44 and horizontally transverse (FIG. 6) to the plane of the lower surface of locator plate 41 and, thus, is transverse to the central long axis of main body 15. In the preferred embodiment shown, the distance between the center of passage 44 and planar surface 49 of FIG. 4 is 0.812" (20.6 mm). In the preferred embodiment shown in FIG. 4, holder 40 is 3.06" (77.7 mm) in its longest dimension and 0.76" (19.3 mm) in its shortest dimension. In the preferred embodiment shown in FIG. 5, locator plate 41 is 0.25" (6.4 mm) in thickness and is 0.375" (9.5 mm) above the lower edge of guideplate 43, raised portion 42 is 0.63" (16 mm) in height and guideplate 43 is 0.38" (9.7 mm) in thickness. In FIG. 6, the preferred embodiment of guideplate 43 shown is 1.5" (38.1 mm) in height and 0.75" (19.1 mm) in width with passages 45 and 50 being 0.25" (6.4 mm) in diameter and are spaced 1" (25.4 mm) apart.

FIGS. 7-9 show a preferred embodiment of a distal femoral condyle resection guide instrument 70. Instrument 70 has a recessed portion 71 which is adapted to cooperatively engage the front surface 49 and sides of guideplate 43 shown in FIG. 6. A locking bolt or other means is passed through slot 72 in portion 71 to secure instrument 70 to holder 40 as shown in FIG. 14. Portion 71 has resection guides 75 and 76 attached to it by means of arms 74 and 73, respectively. Arms 74 and 73 hold the guide surfaces 77 and 78, respectively of resection guides 75 and 76 at a fixed and preselected distance from and parallel to the central long axis of passage 44. At the same time, guide surfaces 77 and 78 are held in a position which is transverse to the central long axis of main body 10 (not shown).

Since the central long axis of passage 44 is adapted to be concentric with the central long axis of passage 17 in main body 10, the position of the guide surfaces 77 and 78 of guideplates 75 and 76 which are distal to recessed portion 71 and which are used to guide a resection means such as a saw blade are situated along the distal femoral condyles relative to the position of the central long axis of passage 17. As can be seen in FIG. 13, a locator pin 129 having handle 131 and having a positioning portion 130 which is adapted to cooperatively engage with passage 17 is passed through passage 17 and main body 10 and is moved toward the proximal end of the femur until the rear surface of portion 130 rests in the middle of and against the distal intercondylar notch 135 of distal femur 134. As a result, the guide surfaces 77 and 78 are spaced away from notch 135 a distance equal to the distance between a plane formed by guide surfaces 77 and 78 of guideplates 75 and 76 and the central long axis of passage 17 plus an amount equal to the radius of portion 130 (0.250" (6.35 mm) in diameter when passage 17 is 0.257" (6.53 mm) in diameter) because the central long axis of portion 130 is adapted to be concentric with passage 17. The actual distance selected is dependent upon the configuration of the distal femoral prosthesis for which the distal femoral surface is being shaped to receive. Instrument 70 enables a surgeon to easily and reproducibly resect the distal femoral condyles of both the right and left femur using the same guide instrument 70 and the resection is always made relative to the distal intercondylar notch and transverse to and at a preselected angle with respect to the central long axis of the femur. Another advantage is that the alignment guide is noninvasive, i.e., it is not affixed to the femur by boring holes or by using other fixation means which extend through the surface of the femur.

FIGS. 10-12 show a preferred embodiment of an anterior-posterior condyle resection guide instrument 100 which contains a recessed portion 101 which is adapted to cooperatively engage the front surface 49 and sides of guideplate 43 of FIG. 6. A locking bolt or other means is passed through slot 102 to holder 40 as shown in FIG. 15. Recessed portion 101 functions in the same manner as does the previously described recessed portion 71 of instrument 70. However, portion 101 further includes passage 103 which is also adapted to cooperatively engage a locator pin 129 having positioning portion 130 as shown in FIG. 15 such that the rear portion of positioning portion 130 is inserted through passage 103 up to handle 131 and instrument 100 is lowered until the rear surface of portion 130 contacts the anterior surface of the femur 150 located in the intercondylar notch between the anterior aspects of the lateral and medial femoral condyles. The distance between the lower surface of portion 103 and the upper surface of guideplate 104 is selected to suit the requirements of the distal femoral prosthesis for which the distal femoral surface is being shaped to receive because the upper surfaces of guideplate 104 located on either side of portion 101 are employed as resection guide surfaces upon which a resection means such as a saw blade is placed to accomplish resection of the anterior aspects of the medial and lateral femoral condyles. The lower surface of guideplate 104 is likewise located at a preselected distance from the lower surface of positioning portion 130 which suits the requirements of the distal femoral prosthesis selected and those lower surfaces are used to guide a resection means in resecting the posterior aspects of the medial and lateral femoral condyles. The rear surface of guideplate 104 is parallel to the central long axis of passage 17 of main body 10 and is thus transverse to the central long axis of the main body 10 and of the femur. Bevel cutting guides 105 and 106 are located in guideplate 104 in such a manner that the anterior distal femoral aspects of the femoral condyles are resected at an angle 9 as shown in FIG. 11. In the embodiment shown, angle 9 is 45° with respect to an extension of slot 106 and the rear surface of guideplate 104. The location of slots 105 and 106 relative to the lower surface (contacting the femur) of positioning portion 130 as well as the angle 9 will be dictated by the type of distal femoral prosthesis selected to be affixed to the distal femoral surface.

Passages 107 and 108 act as guides for the boring of holes in the distal femoral surface to receive distal femoral prosthesis fixation studs which are used to hold the selected distal femoral prosthesis to the femur and their location on guideplate 104 is likewise dictated by the prosthesis selected. It is another advantage of the present invention that instrument 100 and the other apparatus described herein can be used to shape the distal femoral surface of both the left and the right femur.

Distal femoral prostheses are well known to those skilled in the art as shown in the previously noted Howmedica, Inc. brochure and no specific details as to their design are included herein. It is well within the ability of those skilled in the art to construct guide instruments in accordance with the aforementioned description which meet the specific design requirements to produce a shaped distal femoral surface for a particular distal femoral prosthesis.

The above described main body, locator plate, resection instruments and components thereof are all preferably manufactured from a suitable surgical grade of stainless steel of the type commonly employed by those skilled in the art to construct surgical tools for use in contact with the body. The exact composition of the metal from which the above are constructed forms no part of the present invention and other metals suitable for use within the body and for the intended uses of the instruments may be used without altering the nature of the invention.

The manner in which the method of the present invention may be carried out will now be described. The pre-operative procedures for radiographically determining the central long axis of the femur and the angle at which resection of the distal femoral surface is to be made with respect to that axis (physiological valgus) using this method is the same as is typically employed in other methods known to those skilled in the art. Deformities in the femur are also noted during this procedure.

Operatively, the extremity is prepared and draped in the usual manner. An anterior 5" to 6" (127 mm to 152 mm) midline incision is made with the knee flexed to 90 degrees. The knee is then placed in extension and dissection is carried out in line with the skin incision down through the medial retinaculum. Subperiosteal flaps are developed medially and laterally about the metaphyseal flares. The patella is reflected laterally and the knee is flexed to 90 degrees. The anterior portion of the menisci are excised and the anterior cruciate ligament is incised.

If a proximal tibial prosthesis is to also be implanted as in total knee implant surgery, the proximal tibial surface may preferably now be shaped to receive that proximal tibial prosthesis in the manner typically employed for such a prosthesis. The tibial surface should be prepared such that the tibial prosthesis will properly align and cooperate with the distal femoral prosthesis which is attached to the distal femoral surface being shaped in accordance with the method of the present invention.

After the proximal tibial surface has been shaped, the knee is placed in extension and a "T" incision is made in the synovial recess off the anterior femur. A plane is developed between the soft areolar tissue and the periosteum. Care should be taken not to strip the periosteum from the anterior portion of the femur.

The aforementioned surgical procedure is not illustrated. The following operations can be followed by referring to FIG. 13 which illustrates the end result of these operations. Locator 40 is cooperatively engaged with main body 10 by inserting holder 16 through passage 44 and locking bolt 133 is passed through the appropriate passage in locator plate 41 corresponding to the desired degree of valgus radiographically determined to be needed for the patient. Typically, an angle of 5°, 7°, 9°, or 11° will suffice with 9° being the most commonly used degree of valgus. Locator plate 41 is rotated about holder 16 until the correct passage (18 for the right and 19 for the left femur) in main body 10 lines up with passage 44 and locking bolt 133 is passed into passage 18 or 19 to fix locator 40 to main body 10. Positioning portion 130 of locator pin 129 is placed through passage 17 in main body 10 and main body 10 is then inserted along the anterior shaft of the femur with fins 11 and 12 resting along that shaft until positioning portion 130 contacts the distal intracondylar notch 135 and main body 10 cannot be inserted any further.

The central long axis of positioning portion 130 should then be aligned perpendicular to a plane defined by the posterior aspects of the medial and lateral femoral condyles by moving main body 10 from side to side until it is aligned as above. Generally, if there is no angular deformity in the distal femoral surface, the central long axis of positioning portion 130 will point down the shaft of the tibia. The alignment may be checked by placing a straight edge transversely along the posterior surfaces of the femoral condyles to insure that the central long axis of positioning portion 130 is perpendicular to the plane defined by the posterior surfaces of the femoral condyles. This positioning determines the proper rotational alignment for the distal femoral prosthesis to be attached.

Main body 10 with locator 40 attached thereto is then securely fixed to the distal femur 134 by some suitable means such as clamp 136. In FIG. 13, locator pin 129 is shown above passage 17 for the purposes of clarity. Locking bolt 132 which is employed to secure resection guide instruments to guideplate 43 is shown in exploded fashion set away from passage 50. For some distal femoral surfaces, it may be more desirable to place locking bolt 132 in passage 45 instead of passage 50.

The positioning pin is removed and distal femoral condyle resection guide instrument 70 is cooperatively engaged with guideplate 43 of locator 40 and lowered until the arms 73 and 74 rest on the anterior surfaces of the distal femoral condyles and secured to guideplate 43 by means of locking bolt 132. A resection means such as an oscillating saw (not shown) is placed against the distal surface 78 of guide 76 and the saw is brought across the guide 76 in the direction of the arrows shown on surface 78 to transversely resect the distal femoral condyle. The same procedure is repeated for the opposite distal condylar surface using guide 75 to guide a resection means in the direction of arrows 142. Instrument 70 is then removed and the resection of each distal condylar surface is completed if it could not be completed with instrument 70 in place. The resulting resected distal femoral surface is transverse to the central long axis of the femur and offset from that axis by the preselected angle of physiological valgus.

As shown in FIG. 15, anterior-posterior condyle resection guide instrument 100 placed on guideplate 43 and locking bolt 132 is loosely placed in passage 50 such that instrument 100 can slide up and down on guideplate 43 in the direction of the arrows. The prosthesis selected and thus the size of the guideplate 104 of instrument 100 selected should be as large as possible consistent with the size of the distal femur such that the prosthesis to be implanted will provide stability with the knee in flexion. Positioning portion 130 of locating pin 129 is inserted into passage 103 and instrument 100 is lowered until the lower surface of portion 130 contacts the anterior surface of the femur located in the intercondylar notch 150 located between the anterior aspects of the lateral and medial distal femoral condyles. Preferably, the upper surface of guideplate 104 is located relative to the lower surface of portion 140 such that when portion 130 touches the intercondylar notch 150, the upper surface of guideplate 104 is parallel to the apex of the anterior surface of the shaft of the femur 134.

Resection of the distal femoral surface using instrument 100 (not shown) is accomplished by using the upper surface of guideplate 104 as a guide for transversely resecting the anterior aspects of the distal femoral condyles and the lower edge of guideplate 104 is employed as a guide for transversely resecting the posterior aspects of the distal femoral condyles in the direction of arrows 151 and 152. The anterior distal femoral surface is bevelled by placing a resection means in each of the bevelled slots 105 and 106 using the anterior bevelled surface of each slot as a resection guide surface. Fixation stud holes are drilled in the distal femoral surface using holes 107 and 108 in guideplate 104 as a guide. Instrument 100 is removed and any resections which could not be completed with instrument 100 in place are completed. Main body 10 and locator 40 are removed from the femur by releasing clamp 136.

FIG. 16 shows the appearance of distal femur 134 and further shows the last step of bevelling the posterior surface at a preselected angle which is suitable for the distal femoral prosthesis selected. In FIG. 16, oscillating saw blade 160 is employed to bevel the posterior aspect of distal femur 134 at a 45° angle relative to with respect to the distal surface of the femur which is transverse to the central long axis of the femur. For purposes of clarity, only the femur is shown in FIGS. 16 and 17.

FIG. 17 is a perspective view of distal femur 134 which has been shaped in accordance with the method of the present invention. Fixation stud holes 170 and 171 are shown located on the distal femoral surface with the anterior aspect of distal femur 134 shown by reference numeral 172. Bevelled surface 173 is the result of the procedure depicted in FIG. 16.

The preselected distal femoral prosthesis (not shown) and, if one is to be implanted, an appropriate proximal tibial prosthesis can then affixed in accordance with methods known to those skilled in the art. The wound is then closed in the usual fashion employed during the implantation of such prostheses.

Other modifications and variations of the method and apparatus of the present invention will become apparent to those skilled in the art from an examination of the above specification and drawings. Therefore, other variations of the present invention may be made which fall within the scope of the appended claims even though such variations were not specifically discussed above.

That which is claimed is:

1. A method of preparing a human femur having a distal femoral surface containing medial and lateral condyles to receive a distal femoral knee prosthesis, said method comprising the steps of
  (A) placing a main body of an alignment guide in contact with the anterior surface of the shaft of said femur, said main body having a resection guide instrument holder cooperatively engaged thereto and fixedly secured to the main body at a preselected angle with respect to the central long axis of said main body, said main body having at least two separate first means for maintaining a fixed relationship with respect to the anterior distal surface of a human femur, said first means being interconnected in such a manner that the central long axis of the main body can be brought to lie over the central long axis of the femur, said main body further containing a second means for cooperatively engaging the resection guide instrument holder such that the central long axis of the holder can be brought into correspondence with the central long axis of the main body and such that the holder can be pivoted about a transverse axis passing through said central long axis of the main body, said transverse axis approximately paralleling the central long axes of the distal lateral and medial condyles of said femur, said second means further being adapted to cooperatively engage a locator pin in such a manner that the central long axis of the locator pin is coaxial with respect to said transverse axis and said resection guide instrument holder being adapted to cooperatively engage said second means such that the central long axis of said holder can be pivoted about said transverse axis relative to the central long axis of the main body, said holder having a third means located thereon for fixing the central long axis of the holder at a preselected angle with respect to the central long axis of the main body and a guide means for cooperatively engaging a distal femoral shaping guide instrument and maintaining it in a fixed relationship with respect to the central long axis of the main body,
  (B) passing a locator pin through said second means, said locator pin being adapted to be passed through and cooperatively engaged with said second means such that the central long axis of said locator pin is concentric with said transverse axis, said pin further being of a sufficient length to indicate the proper positioning of said main body on the femur when said pin is caused to rest on and aligned in the center the distal femoral intercondylar notch,
  (C) advancing said main body along the anterior surface of the femur until said locator pin contacts the center of the distal femoral intercondylar notch,
  (D) rotating said main body on the anterior surface of said femur until the central long axis of said locator pin is perpendicular to a line defined by the posterior surfaces of the medial and lateral distal femoral condyles, (E) affixing said main body to the anterior surface of the femur, (F) attaching at least one femoral surface shaping guide instrument to said guide holder, said instrument being adapted to cooperatively engage said guide means and to assume an appropriate fixed relationship with respect to the distal femoral surface and to the central long axis of the femur, said instrument being further designed to aid in shaping the distal femoral surface in such a manner that a preselected femoral knee prosthesis can be attached to said surface, and (G) modifying the distal femoral surface through the use of said instrument, (H) repeating steps (F) and (G) as needed until an appropriately shaped distal femoral surface is obtained, using said guide, (I) removing said main body, holder and any guide instrument engaged therewith from the femur, (J) completing any further shaping of the distal femoral surface needed to obtain an appropriately shaped distal femoral surface.

2. The method as claimed in claim 1 wherein at least one shaping guide instrument employed in step (F) is a distal femoral condyle resection guide instrument comprising a recessed portion which is adapted to cooperatively engage said guide means of the holder and maintain said guide in proper alignment with respect to said holder, said guide having a plurality of resection guides for transversely resecting the distal femoral surfaces of the medial and lateral condyles, each of said resection guides being attached to said recessed portion by means of an interconnecting arm, said guides being held transversely to the central long axis of said main body and the femur and further being held at a fixed distance from the intercondylar notch of the femur by means of the position of said main body with respect to said locator pin.

3. The method as claimed in claim 1 wherein at least one shaping guide instrument of said (F) is an anterior-posterior condyle resection guide instrument which comprises a plate having an upper resection guide surface for a resecting means used to resect the anterior aspects of the femoral condyles, a lower resection guide surface for a resecting means used to resect the posterior aspect of the femoral condyles, and a bevel resection guide surface for a resecting means used to resect the medial and lateral distal condyles at a preselected angle, all of said guide surfaces being adapted to resect said distal femoral surface relative to the central long axis of the main body and of the femur, said plate having a recessed portion attached thereto for cooperatively engaging said holder and maintaining said plate in a fixed relationship with respect to the main body, said instrument further having a means located near the upper resection guide surface for receiving said locating pin such that when the locating pin is passed through said means and the instrument is lowered until the pin is allowed to rest in the intercondylar notch between the anterior aspects of the distal femoral condyles, the resection guide surfaces of said plate are aligned with respect to the superior anterior surface of the femur.

4. A distal femoral surface shaping guide comprising the combination of (A) a main body having a central long axis alignable with a femur and at least two separate first means for maintaining a fixed relationship with respect to the anterior distal surface of a human femur, said first means being interconnected in such a manner that the central long axis of the main body can be brought to lie over the central long axis of the femur, said main body further containing a second means for cooperatively engaging a resection guide instrument holder such that the central long axis of the holder can be brought into correspondence with the central long axis of the main body and such that the holder can be pivoted about a transverse axis passing through said central long axis of the main body, said transverse axis approximately paralleling the central long axes of the distal lateral and medial condyles of said femur, said second means further being adapted to cooperatively engage a locator pin in such a manner that the central long axis of the locator pin is coaxial with respect to said transverse axis, (B) a resection guide instrument holder being adapted to cooperatively engage said second means such that the central long axis of said holder can be pivoted about said transverse axis relative to the central long axis of the main body, said holder having a third means located therein for fixing the central long axis of the holder at a preselected angle with respect to the central long axis of the main body and a guide means for cooperatively engaging a distal femoral shaping guide instrument and maintaining it in a fixed relationship with respect to the central long axis of the main body, (C) a locator pin adapted to be passed through and cooperatively engaged with said second means such that the central long axis of said locator pin is concentric with said transverse axis, said pin further being of a sufficient length to indicate the proper positioning of said main body on the femur when said pin is caused to rest on and aligned in the center of the distal femoral intercondylar notch, (D) at least one femoral surface shaping guide instrument which is adapted to cooperatively engage said guide means and to assume an appropriate fixed relationship with respect to the distal femoral surface and to the central long axis of the femur, said instrument being further designed to aid in shaping the distal femoral knee surface in such a manner that a preselected femoral knee prosthesis can be attached to said surface, and (E) a means for affixing said main body to the distal femur.

5. The guide as claimed in claim 4 wherein at least one shaping guide instrument of said (D) is a distal femoral condyle resection guide instrument comprising a recessed portion which is adapted to cooperatively engage said guide means of the holder and maintain said guide in proper alignment with respect to said holder, said guide having a plurality of resection guides for transversely resecting the distal femoral surfaces of the medial and lateral condyles, each of said resection guides being attached to said recessed portion by means of an interconnecting arm, said guides being held transversely to the central long axis of said main body and the femur and further being held at a fixed distance from the intercondylar notch of the femur by means of the position of said main body with respect to said locator pin.

6. The guide as claimed in claim 4 wherein at least one shaping guide instrument of said (D) is an anterior-posterior condyle resection guide instrument which comprises a plate having an upper resection guide surface for a resecting means used to resect the anterior aspects of the femoral condyles, a lower resection guide surface for a resecting means used to resect the posterior aspect of the femoral condyles, and a bevel resection guide surface for a resecting means used to resect a distal portion of the medial and lateral distal condyles at a preselected angle, all of said guide surfaces being adapted to resect said distal femoral surface relative to the central long axis of the main body and of the femur, said plate having a recessed portion atached thereto for cooperatively engaging said holder and maintaining said plate in a fixed relationship with respect to the main body, said instrument further having a means located near the upper resection guide surface for receiving said locating pin such that when the locating pin is passed through said means and the instrument is lowered until the pin is allowed to rest in the intercondylar notch between the anterior aspects of the distal femoral condyles, the resection guide surfaces of said plate are aligned with respect to the superior anterior surface of the femur.

* * * * *